United States Patent [19]

Pascal

[11] 4,366,244

[45] Dec. 28, 1982

[54] METHOD FOR MEASURING SERUM CHOLESTEROL

[75] Inventor: Marc Pascal, Dijon, France

[73] Assignee: Laboratoires Goella, Paris, France

[21] Appl. No.: 243,690

[22] Filed: Mar. 16, 1981

Related U.S. Application Data

[63] Continuation of Ser. No. 53,885, Jul. 2, 1979, abandoned.

[30] Foreign Application Priority Data

Jul. 4, 1978 [GB] United Kingdom ............... 28815/78
Jan. 22, 1979 [GB] United Kingdom ................ 7902255

[51] Int. Cl.$^3$ .................. C12Q 1/60; C12Q 1/26; C12Q 1/46
[52] U.S. Cl. .................................. 435/11; 252/408.1; 260/112 B; 260/112 R; 260/123.5; 210/905; 435/20; 435/25; 435/810; 23/909
[58] Field of Search ................ 210/905, 927; 422/61; 435/11, 20, 25, 810; 23/230 B, 909; 260/112 B, 112 R, 123.5; 424/101, 177, 2; 252/408 R

[56] References Cited

U.S. PATENT DOCUMENTS

| | | | |
|---|---|---|---|
| 3,839,314 | 10/1974 | Fekete et al. | 210/927 |
| 3,902,964 | 9/1975 | Greenspan | 210/905 |
| 3,955,125 | 5/1976 | Proksch et al. | 260/112 B |
| 4,096,136 | 6/1978 | Ayers et al. | 260/112 B |
| 4,110,077 | 8/1978 | Klein et al. | 260/112 B |
| 4,126,416 | 11/1978 | Sears | 23/230 B |
| 4,148,869 | 4/1979 | Deaton | 260/112 B |
| 4,188,188 | 2/1980 | Willner et al. | 435/11 |

OTHER PUBLICATIONS

Chemical Abstracts, vol. 81, 87328g, (1974).
Burstein M., et al., "Rapid Method for the Isolation of Lipoproteins from Human Serum by Precipitation with Polyanions", *Jour. of Lipid Research*, vol. 11, (1970).

*Primary Examiner*—Benoit Castel
*Attorney, Agent, or Firm*—Sprung, Horn, Kramer & Woods

[57] ABSTRACT

The invention relates to methods for measuring cholesterol of various fractions of seric lipoproteins, the methods comprising the separation of said fractions of lipoproteins by means of a lectin capable of precipitating the LDL and VLDL fractions, then measuring the amount of cholesterol in the precipitate and in the remaining solution.

23 Claims, No Drawings

METHOD FOR MEASURING SERUM CHOLESTEROL

This is a continuation of application Ser. No. 53,885 filed July 2, 1979, now abandoned.

The invention relates to methods for measuring serum cholesterol.

The part played by cholesterol in cardiovascular disorders has been studied for a long time. Until recently, however, analyses conducted for detecting the risks of appearance of these disorders related essentially, as regards measure of seric lipids, to the determination of the total cholesterol present in the serum.

However, in the field of lipids, the influence of the total cholesterol, or again of triglycerides, on the incidence of cardiovascular diseases has been studied more deeply for some years past by reason of the existence of relatively frequent cases calling in question once more the previously accepted correlation between the total cholesterol content and the appearance in particulaar of coronary thrombosis.

It is known that cholesterol is present in serum in lipoproteins. These do not present themselves in a uniform manner on analysis and the following are distinguished in particular, as a function of standards of density:

lipoproteins of very low density, or VLDLs in accordance with the initials of the British terms serving to designate them ($0.96 < d < 1.000$), lipoproteins of low density, or LDLs ($1.006 < d < 1.063$), lipoproteins of high density, or HDLs ($1.063 < d$).

Recent research for detecting the risk of cardiovascular disorders has been directed towards differentiated measurements of the various categories of lipoprotein cholesterol. From all the work carried out in this direction, it appears that, although the total cholesterol is always an important parameter, it does not, by itself, enable the risk of these disorders to be determined. It seems, in fact, that the essential factor is the level of HDL cholesterol. To reach the best possible evaluation of this risk, it seems that it is necessary to determine the level of HDL cholesterol, on the one hand, and the levels of LDL and VLDL cholesterol (that is the lipoproteins containing the apoproteine B), on the other hand.

A convenient form of representation of the risk of these cardiovascular diseases is constituted by the proportion of the cholesterol of the HDL fraction with respect to that of the LDL and VLDL fractions $$R = \frac{HDL \text{ cholesterol}}{(LDL + VLDL) \text{ cholesterol}}$$

As we have said, the principal methods of measurement generally used in medical analysis laboratories had the aim of determining the level of the total cholesterol. These methods had the advantage of requiring only a minimum of equipment and relatively simple reagents. The research referred to above having shown the inadequacy of this type of analysis, new types have been tested with more or less success.

It has been proposed in particular to measure the cholesterol of the B-lipoproteins (LDLs) after isolating them by precipitation with the aid of heparin in the presence of divalent cations. This separation technique has the disadvantage, in the best case, of not being sufficiently specific. The result of this is generally too great an inaccuracy with regard to the level of HDL cholesterol for it to be permissible to use this method for evaluation of the risks, and in particular of the previously indicated factor R.

At the present time, the sole means available for effecting the separation and measurement of the various lipoproteincholesterol fractions under satisfactory conditions of precision are based on methods of ultracentrifuging carried out on a medium presenting a density gradient.

The equipment required for this kind of operation is very costly and has no other use in medical analysis laboratories. Moreover, the use of these methods of separating lipoproteins is a relatively long process and this adds to the cost and limits the number of analyses possible in a given time.

For all these reasons, measurements of cholesterol for determining in the best possible way the factors of risks of vascular diseases as they have become apparent in the course of recent research are carried out only exceptionally, whereas their great advantage would justify systematic use.

Consequently, an object of the invention is to provide methods for determining the factors of risks of cardiovascular diseases connected with variations in the levels of serum cholesterol and which do not present the disadvantages of previous methods.

In particular, it is an object of the invention to provide methods for measuring the serum cholesterol per fraction of lipoproteins by means which are accessible to any medical analysis laboratory without entailing costly investment. The invention also relates to methods enabling measurements to be achieved whose duration and cost are compatible with the use of systematic detection or checks.

In order to arrive at such methods, the Applicant first endeavoured to find a technique of separation of the serum lipoproteins which would be sufficiently specific while retaining the advantage of relatively simple use. After various researches, the Applicant has discovered that a technique meeting these requirements consists of separation by selective precipitation of the LDL and VLDL liproprotein fractions (the lipoprotein containing the apoprotein B) by adding lectins to the serum samples investigated.

Earlier studies had shown the interaction of lectins, fixed to a material filling a chromatography column, with serum lipoproteins.

The interaction of lipoproteins and lectins has been confirmed by study of the effect of the lipoproteins on the agglutinability of erythrocytes which is induced by the lectins.

The Applicant has studied this interaction between lectins and lipoproteins and has shown that it can lead to separation of the HDL fraction, on the one hand, and the LDL and VLDL fractions on the other hand, by precipitation of the latter, and that this precipitation can meet the conditions of specificness required to permit sufficiently precise measurement of the cholesterol belonging to these fractions. Due to this discovery, the Applicant has been able to achieve the aims which he intended to achieve.

The method of measuring serum cholesterol according to the invention comprises separation of the LDL and VLDL lipoproteins, on the one hand, and the HDL lipoproteins, on the other hand, and then determination of the amount of cholesterol contained in at least one of the two fractions. Preferably, determination of the cholesterol content is carried out on the two separated fractions. This method is characterised in that separation of the two fractions of lipoproteins is obtained by selective precipitation by means of a lectin capable of forming insoluble complexes with the lipoproteins of low density.

The chemical or physicochemical mechanisms which cause the LDL and VLDL lipoproteins to be precipitated by certain lectins, whereas, under the same conditions, the HDL lipoproteins remain soluble have not been completely elucidated. The research carried out more particularly by the Applicant shows sufficiently, however, that it is possible to obtain a very specific action on the serum lipoproteins as a function of their density with certain lectins (also called phytohaemagglutinins). In this type of selective reaction, leading in particular to the formation of insoluble complexes, the assumption may reasonably be expressed, taking account of the state of present knowledge, that these lectins have an affinity for certain special sites present in the lipoproteins in question. These sites are in particular osidic patterns.

Taking account of these hypotheses, preferred lectins are those which show an affinity for the patterns in question and in particular galactose residues.

Be that as it may, the choice of the lectins used for carrying the invention into effect is based essentially on practical criteria. For the expert, it will consist essentially in verifying, among the lectins available, those which precipitate these lipoproteins having low densities containing the apoprotein B (LDL and VLDL) without precipitating the lipoproteins of high densities (HDL).

Among the lectins usable, concanavalin (lectin extracted from *Canavalia ensiformis*) is particularly advantageous for carrying the invention into effect, but other lectins may be used.

In order to lead to the separation of the lipoproteins, it is a matter of course that the amount of lectin added must be sufficient, taking account of the size of the serum sample treated. The concentration conditions also intervene in the shifts in the chemical equilibria which are the origin of the reaction of precipitation of complex compounds.

Thus, the addition of a lectin to a serum sample, the whole being greatly diluted, may lead to incomplete precipitation of the lipoproteins of low density even if, otherwise, the amount of lectin used should be sufficient to precipitate the whole of these lipoproteins.

On the other hand, in very concentrated medium, the precipitation, which is effected on a priority basis on the lipoproteins of low density, may extend to part of the lipoproteins of high density.

For simplicity and reproducibility of measurement, it is preferable to carry out a practically complete separation of the two types of lipoproteins which we have distinguished. Therefore, for each lectin used, the range of concentration is used for which the precipitation of the LDL and VLDL lipoproteins is complete and that of the HDL lipoproteins is practically speaking nil.

As regards concanavalin in aqueous solution, when the serum samples investigated have not undergone prior dilution, an advantageous range of concentration is between about 0.8 mg/ml and 3 mg/ml. Preferably, a solution containing about 1 mg/ml is used.

By way of indication, as regards concanavalin, solutions whose concentration is equal to or higher than 10 mg/ml produce the precipitation of a not inconsiderable part of the HDL lipoproteins present in the serum which may reach 10%.

The reactions envisaged in the method according to the invention, bringing into play the shift of chemical equilibria, are not instantaneous. It is therefore necessary to maintain the reaction mixture until the formation of the insoluble complex is practically complete. At room temperature and under the preferred conditions, the reaction can be regarded as complete after 1 hour.

In the treatment of some sera samples, particularly the sera the content of triglycerides of which is especially high (more than 10 g/l, to compare with the content considered as normal and which is 0,5–1,5 g/l), incomplete precipitation of the lightest part of lipoprotein may occur. The proportion of unprecipitated light lipoproteins is always small but when titrated with HDL it may entail a sensible error in the calculation of the above-mentioned ratio.

To prevent from such an error, it has been found that complete precipitation of the light density lipoproteins may be achieved by adding to the precipitation mixture a sufficient amount of a polymer which is hydrosoluble, neutral, polar and have no tensioactive properties. Such polymers modify the polarity of the solution increasing the insolubility of these lipoproteins. Preferred polymers which can be used for this purpose are notably polyethylene glycol or polypropylene glycol polymers. Most preferably polyethylene glycol polymers are used the average molecular weight of which is from 200 to 20000. Such polymers are added in such amount that their content in the mixture is from 0,5 to 5 w. %.

Another advantage of using these polymers is that the time necessary to complete the precipitation is considerably shortened.

The use of the said polymer is advantageous in all the processes in which separation of lipoproteins is achieved by precipitation of the light and very light density fractions. This polymer is particularly efficient in the precipitation by means of lectins however it is also useful in precipitation with systems such as polyanions (heparin and metallic ions for example). In any case, the precipitation of the lightest lipoproteins is improved.

The precipitation being achieved, the separation of the precipitate containing the lectin-lipoprotein (LDL and VLDL) complex from the reaction mixture in which remain in particular the HDL lipoproteins is effected in the conventional manner and by conventional means of separating a precipitate. For convenience of operation, in view of the fineness of the particles in suspension in the mixture, it is advantageous to effect centrifuging and then separate the liquid from the solid residue adhering to the tube. Moderate or average centrifuging such as can be obtained with usual laboratory equipment is sufficient to separate the particles in suspension. For example; centrifuging at 1800 g for 10 minutes permits complete separation.

In any case, this separation obviously has nothing in common with separation operations which are effected for separating the proteins directly as a function of their density. In the case of the proteins, in fact, it is necessary to operate in a medium having a density gradient and subject the sample to very intense centrifuging (ultracentrifuging) requiring very special equipment.

Once the lipoproteins have been separated as has just been indicated, each fraction can be analysed by known methods for measuring serum cholesterol, in particular by colorimetric or chemical methods or biochemical methods such as those in which one or more enzymatic reactions are carried out.

It is necessary, in any case, to use the separated constituents (precipitate and supernatant liquid) under conditions such that the lectin used, concanavalin in the preferred embodiment, and, if need be, the constituents of the serum other than the lipoproteins combined with the cholesterol do not disturb measurement of the cholesterol.

According to the process chosen for the titration, the preparation of the lipoprotein fractions may vary substantially. Two processes particularly advantageous are described hereinafter in more details: a process in which cholesterol is titrated after being separated from the serum constituents which otherwise could possibly interfere, a process in which cholesterol is enzymatically treated and the resulting compounds titrated.

I Separation and titration of cholesterol

Advantageously, the cholesterol of the lipoprotein fractions still in solution is isolated by precipitation before proceeding with its measurement.

According to the invention, it is advantageous to carry out denaturation of the proteins present in the two separated fractions, this denaturation extending of course to the lectin which has served for the selective precipitation. In the case of the supernatant liquid, denaturation of the proteins causes their precipitation and, with it, that of the cholesterol which is combined with them.

In order to effect this denaturation, means which are conventional in the chemistry of proteins are used. In particular, it is advantageous to denature the proteins, without any risk of affecting the lipid elements, by means of acid solutions. Among the acids usable, it is preferred to use trichloroacetic acid (in a concentration higher than 5% and advantageously of the order of 10%), which is known for its denaturing action on proteins, globulins, albumin, etc.

After denaturation of the kind which has just been mentioned, two precipitated solid fractions are available and these can be isolated in conventional manner, in particular by centrifuging.

Advantageously also, the lipoproteins of the supernatant liquid originating from the fractionated precipitation may be isolated from aqueous serum residues by extraction with the aid of solvents which are immiscible with water and are used ordinarily in delipidation techniques. The extracted lipoproteins can then be isolated by driving off the solvent.

In addition to the proteins, other constituents of the serum are capable of interfering with the methods of measuring the cholesterol, in particular in the case of colorimetric measurements.

Thus, it is preferable to eliminate the non-cholesteric chromogenic substances still present, and in particular bilirubin or urea derivatives, from the residues recovered after denaturation of the proteins or extraction with solvent and which contain the cholesterol.

According to an advantageous method in accordance with the invention, selective solubilisation of the cholesterol which leaves the chromogenic substances in the insoluble state is carried out.

The solubilisation of the cholesterol can be obtained by means of solvents such as glacial acetic acid. According to the invention, in order to improve the specificness of the solubilisation and the sensitivity of the method, or, in other words, in order to eliminate from the solution the substances liable to hinder subsequent measurement, it is advantageous, as proposed by Bhandaru R. R. and colleagues (Lipids, 12, 1078 (1977) to add uranyl acetate, known to be an excellent protein stabilizer, to the acetic acid. Acetic acid alone, in fact, would have a tendency to cause solubilisation of the proteins. It is particularly preferable to use a solution containing about 0.2 mg/ml of uranyl acetate in glacial acetic acid.

Starting from the cholesterol solutions corresponding to the two fractions separated initially and then freed from the substances which could make some methods of measurement difficult or insufficiently accurate, quantitative analysis can be performed in conventional manner.

For reasons of convenience, it is usually preferred to determine the cholesterol by colorimetric measurement. Among the various methods known for this measurement, that described by Zlatkis and Zak. (Anal. Biochem., 29, 143 (1969), which allows rapid and highly reproducible operation, is preferred. Moreover, this method has the advantage that it can be applied to very small amounts of samples of the order of less than 20 $\mu$g and even as low as 5 $\mu$g.

For this method, orthophthaldialdehyde in solution in a mixture of acetic acid and sulphydric acid is used as reagent.

II Enzymatic treatment and titration

Various methods for the titration of cholesterol are known which involve enzymatic reactions. These methods may be used to carry out the determination of cholesterol content in the two lipoprotein fractions separated according to the process of the invention. Among these methods are particularly preferred those described by TRINDER P. (J. Clin. Path. 22, 246, 1969) and by RÖSCHLAU P. et al. (Z. Klin. Chem. Klin. Biochem. 12, 403, 1974). In these two methods, the principle is as follows:

hydrolysis of cholesterol with cholesterol esterase,
oxidation of cholesterol with cholesterol oxidase leading to
cholestenone and $H_2O_2$,
titration of $H_2O_2$ by spectrophotometry.

Whichever the enzymatic method chosen, the lipoprotein fractions recovered after the separation stage have to be prepared for proper handling.

The precipitate must be dissolved. This may advantageously carried out with a glucoside solution, notably with a solution of $\alpha$-methylglucopyranoside. Other glucides may be used such as: mannose, galactose, glucose... Besides the solution of the precipitated lipoprotein, the glucoside allows the possible interactions between the lectin and other glycoproteins used in the course of the titration, for example peroxidase, to be avoided.

A surfactive agent is also advantageous to keep the cholesterol in solution. A preferred surfactive agent is Triton×100 (Triton is a registered trade mark) but other may be used such as hydroxypolyethoxydodecane.

Control of the ionic strength of the solution is also advantageous. This may be achieved in a conventional manner by adding a saline solution, for example of sodium chloride, potassium chloride or by use of an appropriate buffer.

Other compounds, which may be useful in the subsequent titration stage, may be added with the preceding ones, for example methanol which is necessary for the enzymatic reactions to be carried out.

When the lipoprotein fractions are in the thus prepared solutions, the usual proceedings may be followed for the enzymatic titration.

According to the invention, whatever the method of determination used after the separation of the fractions of lipoproteins, quantitative analysis is achieved of at least one of these fractions and preferably of both. It is then easy, in order to determine the risk of vascular disease and in particular the risk of atherosclerosis, to establish the ratio of (LDL+VLDL) cholesterol to HDL cholesterol and compare it with statistical values for normal subjects and subjects affected by these disorders.

While carrying out the separation prescribed according to the invention, it is also possible to measure only one of the isolated fractions and combine this measurement, for example, with a conventional method of determining the total cholesterol to arrive, by taking the difference, at the missing value. It is preferable, however, to carry out the measurements on the two isolated fractions and by the same method, this tending to limit the effect of systematic errors on the total result.

The equipment required for carrying the method of measuring cholesterol according to the invention into effect is relatively simple and does not go beyond the usual equipment of ordinary medical analysis laboratories in which haematological analyses are carried out. In particular, in order to effect separation, it is sufficient to use a low-power centrifuge and, for the measurement proper, for example, a conventional spectrocolorimeter is quite suitable.

The reagents required for performing the method according to the invention, and in particular the lectins, do not always figure among the agents which are usual in laboratories working on the simplest routine analyses. Consequently, in order to facilitate performance of this method, the invention also relates to a kit of reagents useful for carrying the method according to the invention into effect. The kit according to the invention is all the more necessary as, in order to achieve reliable and reproducible results, the quality of the reagents must be constant from one measurement to another.

The reagent most liable to changes of quality likely to jeopardize measurement is the lectin. Left in the light or in contact with the atmosphere of the laboratory without special precautions, lectins may become degraded, in particular when they are in solution. In order to ensure good preservation of the lectin, it is preferable to present it in a lyophilised form and protected from moisture. It is likewise preferable to keep it at a temperature lower than room temperature and of the order of 4° C.

To facilitate preparation of the lectin solution at the time of measurement, the lectin is also preferably presented in the form of measured amounts corresponding to a defined volume of water in order to obtain a solution with a given lectin content corresponding to the values defined hereinbefore and preferably to 1 mg/ml.

Other reagents may enter kits, the nature of which depends on the method of titration chosen.

A For carrying out a colorimetric titration

One kit of reagents according to the invention moveover advantageously may contain uranyl acetate, preferably in the form of a pre-prepared solution in glacial acetic acid. It is particularly preferred for the uranyl acetate solution to contain 0.2 mg/ml of acetic acid.

One kit according to the invention also advantageously contains a colouring reagent enabling the cholesterol present to be shown up and measured by a colorimetric method. Preferably, this reagent is constituted by orthophthaldialdehyde. As regards the latter, it is advantageous to present it in pre-measured form for the preparation of solution in glacial acetic acid as occasion arises. A preferred pre-measured amount corresponds to solutions containing 1 mg/ml of orthophthaldialdehyde in glacial acetic acid.

Advantageously, in one kit according to the invention there also appear one or more standardization solutions containing cholesterol in a medium corresponding, qualitatively and quantitatively, to that in which the analysed samples are present after the operations effected according to the invention, prior to the measurement proper.

According to the preferred conditions, the medium of the standard solutions is constituted by a solution of uranyl acetate in glacial acetic acid containing 0.2 mg/ml.

An advantageous standard solution for convenient comparison with the samples being analysed contains a very precise amount of cholesterol, about 20 $\mu$g/ml, in a solution of uranyl acetate in glacial acetic acid (0.2 mg of uranyl acetate per milliliter of acid).

Other reagents useful for carrying the method according to the invention into effect may also appear in the kit. However, these being substances which are commonly found in analytical laboratories, it will be understood that their presence provides, as a supplementary advantage, only that of providing in the same kit all the compounds that are necessary. Among the substances in question there are in particular the acids or acid solutions useful for denaturing the proteins, in particular, according to a preferred embodiment, solutions of trichloroacetic acid with a concentration equal to or higher than 5%. Also among these substances are the accessory substances for the preparation of reagents as occasion arises or for immediate use and, in particular, glacial acetic acid and concentrated solutions of sulphydric acid when orthophthaldialdehyde is used as colouring reagent.

B For carrying out titration involving enzymatic reactions

One kit according to the invention contains advantageously solutions containing separately a glucoside such as α-methylglucopyranoside, a surfactive agent, sodium chloride.

(1) Test of specificness of the method of separating lipoproteins by formation of complexes with concanavalin A In these tests, concanavalin A marketed by the Company PHARMA-INDUSTRIE was used.

The precipitation of the lipoproteins from human serum by concanavalin A was studied in three materials. The first (fraction A) was constituted by complete human serum. The second and third materials were constituted by fractions obtained from the same serum and isolated by the method described by Havel and colleagues in J. Clin. Invest. 34, 1345 (1955).

In accordance with this method, there were separated and isolated by centrifuging a fraction with a density between 1.107 and 1.22 (fraction B) and a fraction with a density below 1.063 (fraction C).

Analysis of the fractions B and C by electrophoresis on a polyacrylamide gel showed that they contained exclusively, in the case of the first, lipoproteins of the so-called HDL type and, in the case of the second, lipoproteins of the so-called LDL and VLDL types.

The capacity of concanavalin A for precipitation was determined for different concentrations and for more or less dilute serum samples.

The precipitation was measured by optical density at a wavelength of 450 nm. At this wavelength, neither the different serum constituents, nor concanavalin A adsorb.

Once the addition of concanavalin A to the various fractions had been made, the precipitate, when there was one, and the supernatant liquid were separated and analysed by electrophoresis on polyacrylamide gel as before.

The results obtained are as follows:

(a) The appearance of the precipitate depends principally on the fractions in question, but also, to a certain extent, on the concentration conditions in which the tests are performed.

With a solution of concanavalin A containing 1 mg/ml, which has proved to be a reagent very suitable for the type of separation sought, precipitation is observed solely in fractions A and C. Analysis under these conditions does not enable any formation of precipitate to be detected in fraction B.

(b) Still using the solution of concanavalin A containing 1 mg/ml, it is found that the amount of precipitate formed is a function of the amount of solution added. For undiluted serum or for dilutions up to 1/25, the relationship of precipitate to amount of concanavalin A solution is practically linear.

(c) Analysis of the supernatant fraction after completion of the precipitation shows, in particular in the case of fraction C, a complete absence of lipoproteins of low density. Consequently, under the conditions indicated, concanavalin A permits practically complete precipitation of these lipoproteins.

Comparison between the tests made on fractions A and C, that is to say between that corresponding to the complete serum and that containing only the LDL and VLDL lipoproteins, shows that the addition of concanavalin A causes the precipitation of these lipoproteins, but also that of other serum proteins.

It is therefore not possible, starting from a complete serum sample, to envisage a method of measurement, for example by optical density at 450 nm, leading directly to the determination of the LDL and VLDL lipoprotein contents.

(d) Still under the conditions indicated, that is to say with precipitation conducted with the aid of a solution containing 1 mg/ml, it was made certain that, in the precipitate obtained from the complete serum, the HDL lipoproteins were not jointly precipitated, even partially (this besides the fact that no precipitate is found with fraction B). For this purpose, the precipitate obtained is redissolved with the aid of a 0.2 M solution of α-D-methyl-glucopyranoside. The affinity of the lectin for the saccharide residues of the lipoproteins is then masked by the presence of these additional sugars and the precipitated complex is redissolved. As regards the lipoproteins electrophoresis of the solution obtained in this way permits the presence of the B-lipoproteins alone, that is to say the LDL and VLDL fractions, to be established.

(e) When the concentration of the solution of concanavalin A is reduced with respect to the preferred solution hereinbefore indicated, the preceding observations are met with again, with the exception of those relating to the fact that the precipitation of the LDL and VLDL lipoproteins is total. If the concentration is too low, in fact, part of these lipoproteins may remain in solution in the supernatant liquid with the HDL lipoproteins.

In the same way, when the concentration of concanavalin A exceeds a certain threshold, there is a tendency to precipitate not only the lipoproteins of low density, but also a part, increasing with the concentration, of the HDL lipoproteins.

In practice, in order to avoid appreciable precipitation of the complex with the HDLs, it is preferable to maintain the solution at less than 10 mg/ml.

Whether all the VLDLs and LDLs are not precipitated or whether part of the HDLs is precipitated, measurement remains practicable since the conditions are reproduced in a constant manner and a correction factor can be determined beforehand. It is preferable, however, to remain in the range in which both the precipitation of the LDLs and VLDLs is practically complete and the HDLs remain in solution.

The foregoing results show the specificness of the method of separating the lipoproteins. It was also made certain that the cholesterol levels of the fractions isolated in this way fully corresponded to those which can be determined after separation effected by ultracentrifuging. In other words, it was verified that the proposed method of separating the lipoproteins is compatible with cholesterol measurement.

In particular, it has been shown that the sum of the cholesterol contents of each of the fractions isolated by following the procedure of the invention described hereinafter in section (2) fully corresponds to the value found for the total cholesterol by applying a conventional measuring method.

(2) Example of carrying into effect of the method according to the invention

To conduct the measurement of the cholesterol of the LDL and VLDL and the HDL fractions, the following reagents were used:

reagent A: solution containing 1 mg/ml of concanavalin A in physiological serum to be prepared as occasion arises, reagent B: aqueous solution containing 10% of trichloroacetic acid, reagent C: solution containing 0.2 mg/ml of uranyl acetate in glacial acetic acid, reagent D: solution containing 1 mg/ml of orthophthaldialdehyde in glacial acetic acid, to be prepared as occasion arises and to be kept sheltered from light, reagent E: concentrated sulphydric acid, standard solution: solution containing 20 µg/ml of cholesterol in reagent C.

The method comprises the following stages: selective precipitation and separation of the lipoprotein fractions, elimination of the undesirable constituents from each isolated fraction, and measurement of the cholesterol in each of the fractions.

(a) Separation of the fractions 0.03 ml of human serum is added to 1 ml of reagent A in a haemolysis tube (tube I). After agitation, the mixture is left to stand for 1 hour at room temperature so that the reaction may be complete.

The mixture is then subjected to centrifuging at 1800 G for 10 minutes to separate the precipitate from the supernatant liquid.

0.7 ml of supernatant liquid is removed and placed in another haemolysis tube (tube II). The remainder of the supernatant liquid is disposed of by inverting tube I and tapping it to eliminate the drops clinging to the walls. The precipitate remains stuck to the bottom of tube I.

(b) Elimination of the constituents liable to cause interference on measurement 0.7 ml of reagent B is added to each of tubes I and II with the object, in particular, of denaturing the concanavalin present in excess. The tubes are agitated to mix the constituents well and are then centrifuged at 1800 g for 5 minutes.

The supernatant liquids are eliminated by inverting the tubes as before.

2 ml of reagent C are added to each tube and the mixture is agitated vigorously and is then left at rest for 30 minutes and then centrifuged for 20 minutes at 3000 g.

0.4 ml and 1 ml, respectively, are removed from tubes I and II and are placed in test tubes I' and II'.

(c) Colorimetric measurement of the cholesterol in each fraction and comparison with a standard sample and with a solution devoid of cholesterol and treated in equivalent manner (control).

The volume in tube I' is adjusted to 1 ml by adding 0.6 ml of reagent C. 1 ml of this reagent is also introduced into the blank test tube and, likewise, 1 ml of the standard solution is introduced into the fourth tube.

1 ml of reagent D is added to each of the four tubes prepared in this way. They are left to stand for 15 minutes at room temperature and then 1 ml of reagent E is added to each tube. The tubes are agitated vigorously and left to stand for 10 minutes before proceeding with measurement.

The solutions, prepared as has just been indicated, are passed through a spectrocolorimeter in the following hour. The measurements are made at 560 nm by comparison with the control test tube for tubes I' and II' and the tube containing the standard solution.

The cholesterol levels of the two separated fractions are expressed, as a function of the optical densities measured, in the following manner:

$$HDL\ cholesterol = \frac{\text{optical density of tube II'}}{\text{optical density of standard}} \times$$

190.5 in mg/100 ml $$LDL + VLDL\ cholesterol = \frac{\text{optical density of tube I'}}{\text{optical density of standard}} \times$$

333.3 in mg/100 ml

From these results or directly, it is possible to calculate the risk factor hereinbefore defined:

$$R = \frac{HDL\ cholesterol}{LDL + VLDL\ cholesterol} =$$

$$\frac{\text{optical density of tube II'}}{\text{optical density of tube I'}} \times 0.57.$$

Of course, the level of total cholesterol can also be determined.

(3) Example of carrying into effect of the method according to the invention (including enzymatic reaction)

In this example, the following reagents were used:

| Precipitating solution | |
|---|---|
| NaCl | 0.15 M |
| Concanavalin A | 1 mg/ml |
| polyethyleneglycol 6000 | 40 mg/ml |

This solution is prepared when needed. It may be stored 1 month at 4° C.

| Solution L.F. | | |
|---|---|---|
| | | for 1 liter |
| NaCl | 0.3 M | 17.53 g |
| α-methylglucopyranoside | 0.7 M | 135.9 g |
| methanol | 6.475 M | 262.6 g |
| Triton X 100 | 1.4% | 1.4 ml |

This solution may be kept at room temperature at least 4 months.

Cholesterol reagent

This reagent is prepared by the admixture of three solutions.

| Solution 1: | | |
|---|---|---|
| potassium phosphate buffer | 0.5 M pH 7.7 | 80 ml |
| phenol | 20 mM | 188.2 mg |
| methanol | 1.85 M | 7.5 ml |
| water | for | 100 ml |
| Solution 2: | | |
| potassium phosphate buffer | 0,5 M pH 7,7 | 80 ml |
| methanol | 1.85 M | 7.5 ml |
| 4 amino antipyrine | 2 mM | 40.65 mg |
| water | for | 100 ml |
| Solution 3: | | |
| Peroxydase type II (SIGMA): 4 U purpurogallin | | 40 µg |
| cholesterol esterase (SIGMA): 330 U | | 312 mg |
| cholesterol oxydase (SIGMA): 104 U | | 500 µl |
| solution 1 | for | 1 ml |

The reagent is made of 100 ml of solution 1, 100 ml of solution 2 and 1 ml of solution 3.

The method comprised the following stages: selective precipitation and separation of the lipoprotein fractions, solution of the precipitate, enzymatic reaction for the cholesterol titration of each fraction.

(a) Precipitation and separation 0.03 ml of the sample of human serum (or EDTA plasma) is added to 1 ml of precipitating solution. The mixture is stirred and left to stand for ¼ hour at room temperature.

The mixture is then subjected to centrifuging at 2000 G for 15 minutes to separate the precipitate from the supernatant liquid.

The supernatant recovered is poured in another tube and the first tube is tapped to detach the drops clinging to the walls of the tube when the precipitate remains stuck to the bottom.

(b) Solution 1 ml of physiological serum and 0.4 ml of solution L.F. are added in the tube containing the precipitate. The mixture is stirred and the precipitate is dissolved. To achieve the solution, the mixture is left to stand for 10 minutes.

(c) Enzymatic reactions and titrations

HDL 0.5 ml of supernatant recovered in (a) are added to 0.2 ml of solution L.F. To this mixture, 2 ml of "cholesterol reagent" are added and the mixture is incubated for 30 minutes at 25° C.

The optical density at 500 nm is measured by comparison with a control tube in which the same mixture is prepared, the supernatant sample being replaced by 0.5 ml of physiological serum.

LDL and VLDL 0.7 ml of the solution of the precipitate are added to 2 ml of "cholesterol reagent" and the method is carried out in the same way as above for HDL.

To determine the cholesterol concentration, the results obtained are compared with those of a standard serum titrated in the same conditions (0.04 ml of standard serum + 0.46 ml of physiological serum + 0.2 ml of solution L.F. + 2 ml of cholesterol reagent).

The cholesterol titer is calculated in this manner $$HDL \text{ cholesterol (mg/0.1 l)} = \frac{8}{3} \cdot \frac{o.d. \text{ sample}}{o.d. \text{ standard}} \times C$$

$$(LDL + VLDL) \text{ cholesterol (mg/0.1 l)} = \frac{8}{3} \cdot \frac{o.d. \text{ sample}}{o.d. \text{ standard}} \times C$$

o.d. is for optical density at 500 nm

C is the cholesterol titer of the standard (mg/0.1 l).

The process described hereabove may be modified in the following manner. After the precipitation step, the lipoprotein fractions are treated with only one solution. This solution may be constituted as follows:

| | |
|---|---|
| α-D-methylglucopyranoside | 0.4 M |
| sodium cholate | 20 mM |
| 4-amino-pyrine | 3 mM |
| phenol | 40 mM |
| peroxidase concentration above | 7500 U/l |
| cholesterol oxidase concentration above | 120 U/l |
| cholesterol esterase concentration above | 300 U/l |
| potassium phosphate buffer pH 7.5 | 0.1 M |

The products entering this solution may be kept in the same container when lyophilized. Preferably the enzymes are kept in a separate container.

Another treating solution may be formed similar to the one just described with the exception of sodium cholate which is substituted for a surfactive agent such as those called Triton or Tween 20 present in the solution at the concentration of 1%. When using one of those surfactive agents methanol is added (4 M).

Whichever the treating solution chosen, the processing of the precipitate and of the supernatant solution is carried as follows:

to 0.5 ml of supernatant, 0.5 ml of treating solution are added, to the precipitate are added 0.5 ml of physiological serum and 0.5 ml of the treating solution.

Incubation and titration are the same as above.

As has been seen, the method which has been described in this way requires a minimum of equipment and, in comparison with present techniques calling for ultracentrifuging, it is much faster. An operator using this method in a routine manner can carry out at least some fifty measurements daily without difficulty.

Moreover, the method leads to results with an accuracy at least as good as that achieved by previous techniques such as that employing ultracentrifuging and, compared with these techniques, has the supplementary advantage of requiring only a very limited volume of serum sample (30 μl instead of about 5 ml).

I claim:

1. A method of determining the cholesterol content of LDL and VLDL lipoproteins in a serum containing the same together with HDL lipoproteins which comprises:

(A) contacting the serum with a solution of concanavalin A wherein the concentration of concanavalin A in said solution is less than 10 mg/ml calculated with respect to undiluted serum, in such an amount as to selectively precipitate substantially all of the LDL and VLDL lipoproteins contained in said serum but to leave HDL lipoproteins in the resultant supernatant liquid;

(B) separating said precipitate from said supernatant liquid;

(C) treating said precipitate so as to denature proteins therein which interfere with measurement of the cholesterol content of lipoprotein in said precipitate;

(D) eliminating serum constituents such as bilirubin and urea derivatives which are liable to interfere with the measurement of the content of cholesterol by contacting the cholesterol in the precipitate with a selective solubilizing agent; and (E) determining the cholesterol content of the isolated precipitate.

2. A process according to claim 1 wherein said concanavalin A is added in the form of an aqueous solution.

3. A process according to claim 2, wherein said aqueous solution contains 0.8 mg/ml to 3 mg/ml of concanavalin A calculated with respect to undiluted serum.

4. A process according to claim 1, wherein there is added to serum to which concanavalin A has been added a neutral polar and non-tensioactive polymer.

5. A process according to claim 4, wherein said polymer is employed in an amount of 0.5 to 5 weight percent based upon the weight of said serum.

6. A process according to claim 4, wherein said polymer is a polyethylene glycol or polypropylene glycol polymer, the average molecular weight of which is 200 to 200,000.

7. A process according to claim 1 wherein the denaturation is effected by means of an acid solution.

8. A process according to claim 1, wherein said selective solubilizing agent comprises a solution of uranyl acetate in glacial acetic acid.

9. A process according to claim 1, wherein the cholesterol content of the precipitate is determined by means comprising reacting the cholesterol with an enzyme.

10. A process according to claim 9, wherein the enzymatic determination of cholesterol content comprises hydrolyzing the cholesterol esters contained therein with cholesterol esterase, oxidizing cholesterol with cholesterol oxidates and titrating $H_2O_2$ resulting from the oxidation reaction.

11. A process according to claim 1, wherein the precipitate is dissolved by means of a glucoside solution and thereafter cholesterol content is determined by means comprising reacting cholesterol with an enzyme.

12. A process according to claim 1, wherein a cholesterol fraction is isolated and the content of cholesterol is determined by colorimetry using a coloring agent consisting of orthophthaldialdehyde in solution in a mixture of glacial acetic acid and sulphydric acid.

13. A method of determining the cholesterol content of HDL lipoprotein in a serum containing the same together with LDL and VLDL lipoproteins which comprises:
(A) contacting the serum with a solution of concanavalin A wherein the concentration of concanavalin A in said solution is less than 10 mg/ml calculated with respect to undiluted serum, in such an amount as to selectively precipitate substantially all of the LDL and VLDL lipoproteins in said serum but to leave HDL lipoproteins in the resulting supernatant liquid;
(B) separating said supernatant liquid from said precipitate;
(C) treating said supernatant liquid so as to denature proteins therein which interfere with measurement of the cholesterol content of lipoprotein in said supernatant liquid;
(D) eliminating serum constituents such as bilirubin and urea derivatives which are liable to interfere with the measurement of the content of cholesterol in the supernatant liquid with a selective solubilizing agent; and
(E) determining the cholesterol content of the supernatant liquid.

14. A process according to claim 13, wherein said solution of concanavalin A is an aqueous solution.

15. A process according to claim 14, wherein the aqueous solution contains between about 0.8 mg/ml and 3 mg/ml of concanavalin A.

16. A process according to claim 13, wherein there is added to the serum to which concanavalin A has been added a neutral, polar and nontensioactive polymer.

17. A process according to claim 16, wherein said polymer is employed in an amount of 0.5 to 5 weight percent based upon the weight of said serum.

18. A process according to claim 16, wherein said polymer is a polyethylene glycol or a polypropylene glycol polymer, the average molecular weight of which is 200 to 20,000.

19. A process according to claim 13, wherein the denaturation is effected by means of an acid solution.

20. A process according to claim 13, wherein said selective solubilizing agent comprises a solution of uranyl acetate in glacial acetic acid.

21. A process according to claim 13, wherein the cholesterol content of the supernatant liquid is determined by means comprising reacting cholesterol with an enzyme.

22. A process according to claim 21, wherein the enzymatic determination of cholesterol content comprises hydrolyzing the cholesterol esters contained therein with cholesterol esterase, oxidizing cholesterol with cholesterol oxidates and titrating $H_2O_2$ resulting from the oxidation reaction.

23. A process according to claim 13, wherein a cholesterol fraction is isolated and the content of cholesterol is determined by colorimetry using a coloring agent consisting of orthophthaldialdehyde in solution in a mixture of glacial acetic acid and sulphydric acid.

* * * * *